United States Patent [19]

Engel

[11] 4,450,845
[45] May 29, 1984

[54] DEVICE FOR SHIELDING HUMAN SKIN FROM AMBIENT LIGHT TO FACILITATE TESTS PERFORMED THEREON

[75] Inventor: Rolf R. Engel, St. Paul, Minn.

[73] Assignee: Minneapolis Medical Research Foundation, Inc., Minneapolis, Minn.

[21] Appl. No.: 350,563

[22] Filed: Feb. 22, 1982

[51] Int. Cl.³ .............................................. A61B 5/00
[52] U.S. Cl. .................................. 128/743; 128/132 R
[58] Field of Search ....................... 128/743, 639–640, 128/132 R, 155

[56] References Cited

U.S. PATENT DOCUMENTS

| 2,221,758 | 11/1940 | Elmquist | 128/132 R |
| 2,841,138 | 7/1958 | Laub | 128/743 |
| 3,212,495 | 10/1965 | Osbourn et al. | 128/743 |
| 3,610,238 | 10/1971 | Rich, Jr. | 128/132 R |
| 4,245,630 | 1/1981 | Lloyd et al. | 128/155 |

FOREIGN PATENT DOCUMENTS

| 2909071 | 9/1980 | Fed. Rep. of Germany | 128/743 |
| 6710599 | 2/1968 | Netherlands | 128/743 |

Primary Examiner—Lee S. Cohen
Assistant Examiner—Angela D. Sykes
Attorney, Agent, or Firm—Dorsey & Whitney

[57] ABSTRACT

A device for shielding a portion of human skin to facilitate the performance of tests on the skin. The device includes a first layer adapted to be secured to the skin to be tested with an opening to permit selective access by a testing instrument. A second layer is positioned above the first layer in a manner permitting selective removal of at least a portion of the second layer to permit access to the skin through the opening in the first layer.

7 Claims, 5 Drawing Figures

U.S. Patent    May 29, 1984    4,450,845
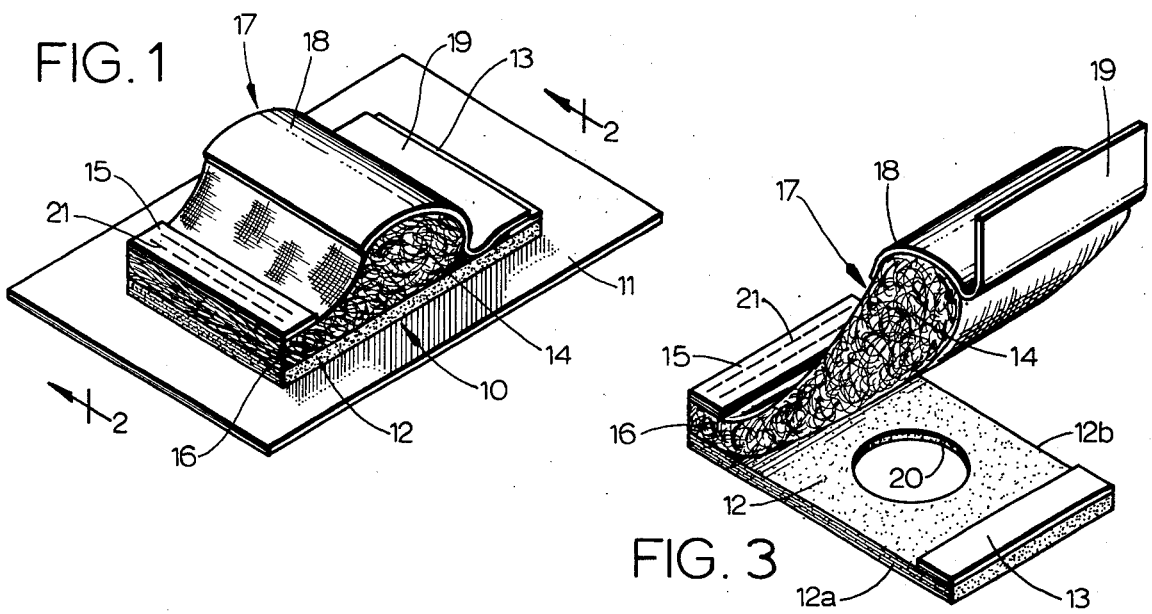
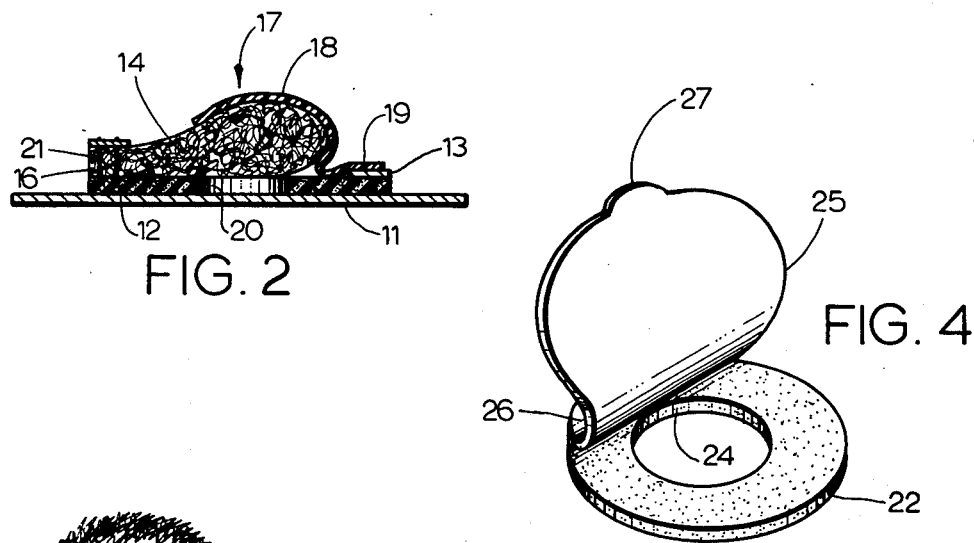
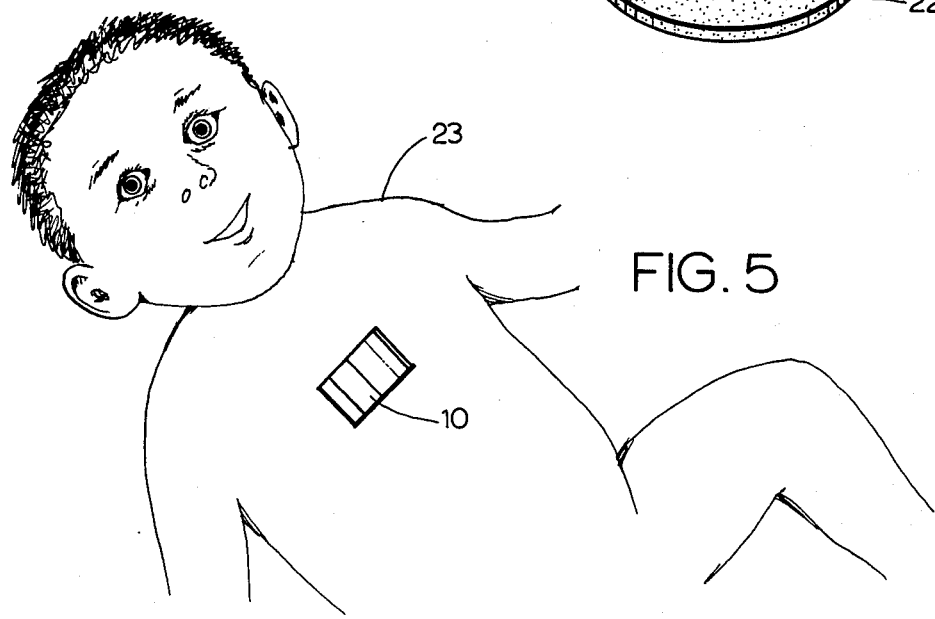

DEVICE FOR SHIELDING HUMAN SKIN FROM AMBIENT LIGHT TO FACILITATE TESTS PERFORMED THEREON

BACKGROUND OF THE INVENTION

The present invention relates generally to a device for shielding the skin of humans from ambient light to facilitate the performance of certain tests on the skin. In a more specific application, the present invention relates to a device for shielding a spot of the skin of infants who are undergoing phototherapy for the treatment of jaundice.

Jaundice is a relatively common occurrence in newborn infants resulting from elevated leves of serum bilirubin. The most common treatment of jaundice or hyperbilirubinemia is the exposure of the infant to phototherapy. This treatment reduces the serum bilirubin concentration. Historically, the only available method for the determination of the serum bilirubin concentration was blood sampling followed by analysis in the laboratory. This, of course, is not only time consuming and relatively expensive, but also requires taking a sample of the infant's blood. A direct relationship exists between a person's skin color or the degree of jaundice and hyperbilirubinemia. This relationship or correlation ultimately led to the development of a cutaneous jaundice meter which utilizes the principles of reflectometry to detect the extent of yellow in the infant's skin which correlates with the level of serum bilirubin. A commercial cutaneous jaundice meter is a hand-held unit having a probe less than one-half inch in diameter which is pressed against the infant's skin. A digital readout provides information with respect to the yellowness of the skin. This jaundice meter is presently indentified by the trademark MINOLTA/AIR-SHIELDS and is distributed by Narco Scientific of Hatboro, Pa.

While the above described jaundice meter has been shown to work satisfactorily with newborn infants for the purpose of mass screening for the determination of the degree of jaundice or the level of serum bilirubin, its usefulness has been questioned with respect to infants undergoing phototherapy for the treatment of such conditions. Specifically, for infants undergoing phototherapy, the relationship between skin color and serum bilirubin levels appears to be disrupted. This is believed to be a result of bleaching and/or tanning of the skin which is a normal occurrence during phototherapy and which affects the accuracy of the jaundice meter reading. Thus, unless the above-mentioned cutaneous jaundice meter can be used to accurately estimate the serum bilirubin level during phototherapy, its value is limited. Accordingly, a need exists for a device which would permit the use of such an instrument during phototherapy.

SUMMARY OF THE INVENTION

The present invention solves the problem outlined above by providing a means which permits the use of a cutaneous jaundice meter for the estimation and monitoring of serum bilirubin levels in infants undergoing phototherapy. The invention is a device which functions to shield a small part of the infant's skin from the effects of phototherapy and to provide access of that small area of skin to the cutaneous jaundice meter for periodic measurements of the intensity of jaundice. As a result, this small area of skin is unaffected by the direct effects of phototherapy such as bleaching or tanning. Thus, the accuracy of the cutaneous jaundice reading, even on infants undergoing phototherapy, is not reduced.

More specifically, the device of the present invention includes a first layer of material with at least one of its surfaces having an adhesive coating to permit it to be secured to the skin of the infant undergoing phototherapy. This first layer has an opening or window to provide access to a small area of the infant's skin. This opening or window should be sufficiently large to allow access by the sensing probe of the cutaneous jaundice meter. The device also includes a second layer designed to overlay the first layer including the opening or window. This second layer is designed for selective removal from at least a portion of the first layer to expose the hole or opening and thus provide access to the skin in the area of the opening for measurement by the jaundice meter. This second layer is preferably constructed of a material which will allow the skin exposed by the opening or window to breathe normally.

Accordingly, an object of the present invention is to provide a device for shielding the skin to facilitate and improve the accuracy of tests conducted on the skin.

Another object of the present invention is to provide a device for shielding the skin to facilitate the use of a cutaneous jaundice meter during treatment of the infant by phototherapy.

A further object of the present invention is to provide a device as described above having means for selectively providing access of a small area of skin to a cutaneous jaundice meter.

These and other objects of the present invention will become apparent with reference to the drawings, the description of the preferred embodiment and the appended claims.

DESCRIPTION OF THE DRAWINGS

FIG. 1 is a pictorial view of one embodiment of the device of the present invention.

FIG. 2 is a sectional view of the device of the present invention as viewed along the section line 2—2 of FIG. 1.

FIG. 3 is a pictorial view of the device of the present invention with the second layer or lid in an up position.

FIG. 4 is a pictorial view of a second embodiment of the device of the present invention showing the second layer or lid in an up position.

FIG. 5 is a pictorial view showing the device of the present invention as applied to the skin of an infant.

DESCRIPTION OF THE PREFERRED EMBODIMENT

Reference is first made to FIGS. 1, 2 and 3 showing a first embodiment of the device of the present invention. In these figures, the device is illustrated generally by the reference numeral 10. More specifically, the device includes a first layer 12 having an adhesive bottom surface to permit securing the device 10 to the skin of the infant. The adhesive surface of the layer 12 is removably secured to a release layer 11. In the first embodiment, the first layer 12 is a generally rectangular shape although other shapes will function satisfactorily. The first layer 12 of the first embodiment is constructed of a foam rubber type material. As shown best in FIGS. 2 and 3, the first layer 12 includes a centrally positioned opening or window 20.

A second layer 14, opaque to the passage of ambient light, is positioned above the first layer 12 and functions to selectively cover the opening or window 20. This second layer 14 in the embodiment illustrated in FIGS. 1, 2 and 3 is connected at its rearward end 16 to the first layer 12. In the first embodiment, this connection is by means of a plurality of stitches 21 (FIG. 2). A strip of tape or other material 15 is placed above the stitches 21 (FIG. 2) to cover the same. A piece of adhesive back tape or other material 18 is secured to a top surface portion of the second layer 14 and extends outwardly from the second layer 14 to form the forwardly extending tab portion 19. The adhesive backed tab portion 19 is adapted for selective adherence to the top surface of the strip 13 which is secured to the top surface of the forward end of the first layer 12. Because of the securement of the second layer 14 to the first layer 12 at the end 16, the second layer 14 acts as a hinged lid 17 with respect to the first layer 12, thus permitting the forward extending tab 19 to be manually lifted to the position illustrated in FIG. 3. The lifting of the lid 17 in this fashion enables the skin in the area of the opening or window 20 to be exposed for purposes of obtaining a reading or measurement by cutaneous jaundice meter of the type previously described. After the reading has been taken, the lid 17 is placed down over the opening 20 and the adhesive backed tab 19 is secured to the strip 13.

In the first embodiment, the second layer is constructed of conventional medical gauze, although it is contemplated that other types of material will also function satisfactorily. It is believed to be important, however, for this material of the second layer to be a material which will allow the skin exposed by the window 20 to breathe in a normal fashion.

The distance between the side edges 12a and 12b (FIG. 3) and the side edges of the opening 20 is also of some importance. If this distance is too small, it is believed that some bilirubin can diffuse laterally from the portion of the unprotected skin during phototherapy, thus resulting in inaccurate readings. It is believed that this distance should be at least two and one-half millimeters.

To use the device of FIGS. 1, 2 and 3, the device 10 is removed from the release layer 11 by peeling off the adhesive-backed first layer 12. The device 10 is then secured to the skin of the infant in the position desired. In some cases, health professionals prefer to secure the device 10 to the forehead of the infant while others prefer to secure the device 10 to the sternum of the infant 23 as illustrated in FIG. 5. The infant 23 can then be exposed to phototherapy for treatment of its jaundiced condition. During periodic measurements to determine the progress of reducing the bilirubin level by phototherapy, the lid 17 (FIGS. 1, 2 and 3) is raised and a measurement taken by a cutaneous jaundice meter. After measurement, the lid 17 is then placed back over the opening to protect the skin test area from the effects of phototherapy.

A second embodiment of the device of the present invention is illustrated in FIG. 4. This embodiment includes a generally annular or doughnut shaped first layer 22 with a central opening or window 24. In this embodiment, the layer 22 includes an adhesive coating both on its bottom surface and its upper surface. The adhesive coating on the bottom surface permits the first layer 22 to be secured to the infant to be tested. The adhesive layer on the upper surface permits the second layer or lid 25 to be selectively secured to the upper surface of the layer 22 to close the opening 24. It should be noted that the stickiness between the bottom surface of the first layer 22 and the skin of the infant should be more aggressive than the stickiness between the upper surface of the first layer 22 and the bottom surface of the lid 25 to prevent the device from being removed from the skin of the infant each time the lid 25 is raised. As illustrated, the second layer or lid 25 is also circular in shape and is fixedly secured to a portion of the first layer 22 at the point 26. The forward edge of the lid 25 includes a tab 27 to facilitate easy lifting of the lid 25. The material from which the lid 25 is constructed is a material which is opaque to the passage of ambient light and will allow the infant's skin to breathe in a normal fashion.

It should also be noted that the device of the present invention can be designed to perform dual functions. For example, it could be designed to also serve as an electrode during conduction of EKG tests, thus minimizing the number of patches needed to be placed on the infant.

Although the description of the preferred embodiment has been quite specific, it is contemplated that various changes and modifications could be made without deviating from the spirit of the present invention. Accordingly, it is intended that the scope of the present invention be dictated by the appended claims rather than by the description of the preferred embodiment.

I claim:

1. A device for shielding a portion of the skin of a human patient to facilitate the performance of tests on the skin via a testing instrument, said device comprising:
   a first layer having a bottom surface and a top surface, said bottom surface having an adhesive layer thereon for adhesion to the skin of the human on which the test is to be performed, said first layer having an opening therethrough to permit selective access by said testing instrument to the portion of the skin exposed by said opening;
   a second, opaque layer positioned above said top surface of said first layer covering said opening and being secured thereto by a hinge means for permitting selective and repeated removal of at least a portion of said second layer from the area of said opening to permit periodic access by said testing instrument; and
   an adhesive coating between said first and second layers, said adhesive coating being effective to adhere said second layer to said first layer despite repeated removals for purposes of testing, said adhesive coating further having adhesive qualities which permit said second layer to be selectively removed from said first layer without removing said first layer from the skin of said patient.

2. The device of claim 21 wherein said second layer is constructed of a material which allows the skin exposed by said opening to breathe in a normal fashion.

3. The device of claim 1 wherein the top surface of said first layer is provided with said adhesive coating.

4. The device of claim 1 wherein said first layer is generally doughnut shaped.

5. The device of claim 4 wherein the distance between the edge of said opening and the outer edge of said first layer is at least two and one half millimeters.

6. The device of claim 1 wherein said second layer includes a tab portion to facilitate easy removal of said portion of said second layer from the area of said opening.

7. The device of claim 1 wherein said first layer is constructed from a foam rubber material.

* * * * *

UNITED STATES PATENT AND TRADEMARK OFFICE
CERTIFICATE OF CORRECTION

PATENT NO. : 4,450,845

DATED : May 29, 1984

INVENTOR(S) : Rolf R. Engel

It is certified that error appears in the above-identified patent and that said Letters Patent is hereby corrected as shown below:

Col. 1, line 15, "leves" should read "levels". Col. 3, line 28, "14" should be added after "layer". Col. 4, line 53, "21" should be "1".

Signed and Sealed this

Fourth Day of December 1984

[SEAL]

Attest:

GERALD J. MOSSINGHOFF

Attesting Officer

Commissioner of Patents and Trademarks